United States Patent
Frazier et al.

(10) Patent No.: US 11,173,296 B2
(45) Date of Patent: Nov. 16, 2021

(54) INTRAATRIAL VENTRICULAR ASSIST DEVICE

(71) Applicant: Texas Heart Institute, Houston, TX (US)

(72) Inventors: Oscar H. Frazier, Houston, TX (US); William E. Cohn, Bellaire, TX (US)

(73) Assignee: Texas Heart Institute, Houston, TX (US)

( * ) Notice: Subject to any disclaimer, the term of this patent is extended or adjusted under 35 U.S.C. 154(b) by 140 days.

(21) Appl. No.: 16/079,910

(22) PCT Filed: Feb. 23, 2017

(86) PCT No.: PCT/US2017/019126
§ 371 (c)(1),
(2) Date: Aug. 24, 2018

(87) PCT Pub. No.: WO2017/147291
PCT Pub. Date: Aug. 31, 2017

(65) Prior Publication Data
US 2019/0054223 A1    Feb. 21, 2019

Related U.S. Application Data

(63) Continuation of application No. 15/052,158, filed on Feb. 24, 2016, now abandoned, which is a
(Continued)

(51) Int. Cl.
*A61M 60/148* (2021.01)
*A61M 60/205* (2021.01)
(Continued)

(52) U.S. Cl.
CPC ........ *A61M 60/148* (2021.01); *A61M 60/205* (2021.01); *A61M 60/414* (2021.01);
(Continued)

(58) Field of Classification Search
CPC .. A61M 1/122; A61M 1/1012; A61M 1/1034; A61M 1/1008; A61M 1/125; A61M 1/101; A61M 1/1086; A61M 1/127
(Continued)

(56) References Cited

U.S. PATENT DOCUMENTS 6,926,662 B1 * 8/2005 Aboul-Hosn ....... A61M 1/3613
600/16
2003/0187322 A1 * 10/2003 Siess ................. A61M 60/419
600/16
(Continued)

FOREIGN PATENT DOCUMENTS

WO    2011/056823 A2    5/2011
WO    2011/056980 A2    5/2011

OTHER PUBLICATIONS

International Patent Application No. PCT/US2017/019126 International Search Report and Written Opinion dated Jun. 2, 2017 (11 pages).
(Continued)

*Primary Examiner* — Mallika D Fairchild
*Assistant Examiner* — Minh Duc G Pham
(74) *Attorney, Agent, or Firm* — Conley Rose, P.C.

(57) ABSTRACT

A medical devices and methods related thereto are disclosed. In an embodiment, the medical device including a pump configured to be inserted within an atrium of a heart, said pump comprising an inlet and an outlet. In addition, the pump includes a flexible outflow conduit coupled to the outlet and configured to carry blood. The outflow conduit includes a radially inner surface defining a throughbore, and a radially outer surface. Further, the pump comprises a driveline configured to conduct control and power signals between the pump and an external device. The driveline
(Continued)

extends through the outflow conduit between the radially inner surface and the radially outer surface.

11 Claims, 11 Drawing Sheets

Related U.S. Application Data continuation-in-part of application No. 12/243,256, filed on Oct. 1, 2008, now Pat. No. 9,504,774.

(60) Provisional application No. 60/976,648, filed on Oct. 1, 2007.

(51) Int. Cl.
| | | |
|---|---|---|
| *A61M 60/414* | (2021.01) | |
| *A61M 60/50* | (2021.01) | |
| *A61M 60/135* | (2021.01) | |
| *A61M 60/857* | (2021.01) | |
| *A61M 60/871* | (2021.01) | |

(52) U.S. Cl.
CPC .......... *A61M 60/135* (2021.01); *A61M 60/50* (2021.01); *A61M 60/857* (2021.01); *A61M 60/871* (2021.01)

(58) Field of Classification Search
USPC .......................................................... 600/16
See application file for complete search history.

(56) References Cited

U.S. PATENT DOCUMENTS

| | | | |
|---|---|---|---|
| 2006/0030864 A1* | 2/2006 | Kennedy, II | A61F 2/97 606/108 |
| 2006/0063965 A1 | 3/2006 | Aboul-Hosn et al. | |
| 2006/0161095 A1* | 7/2006 | Aboul-Hosn | A61M 60/857 604/9 |
| 2007/0208210 A1 | 9/2007 | Gelfand et al. | |
| 2009/0088597 A1 | 4/2009 | Frazier et al. | |
| 2015/0306289 A1 | 10/2015 | Spence | |
| 2016/0166747 A1 | 6/2016 | Frazier et al. | |

OTHER PUBLICATIONS

U.S. Appl. No. 15/052,158 Final Office Action dated Nov. 16, 2017 (13 pages).
European Search Report dated Jul. 12, 2019, for European Application No. 17757205.4 (7 p.).

\* cited by examiner

INTRAATRIAL VENTRICULAR ASSIST DEVICE

CROSS-REFERENCE TO RELATED APPLICATIONS

This application is a National Phase Entry into the U.S. under 35 U.S.C. § 371 of and claims priority to PCT Application No. PCT/US2017/019126, filed Feb. 23, 2017, entitled "Intraatrial Ventricular Assist Device," which claims benefit of U.S. patent application Ser. No. 15/052,158 filed Feb. 24, 2016, and entitled "Intraatrial Ventricular Assist Device," which is a continuation in part of U.S. application Ser. No. 12/243,256 (now U.S. Pat. No. 9,504,774), filed Oct. 1, 2008, and entitled "Intraatrial Ventricular Assist Device," which further claims priority to U.S. Provisional Application Ser. No. 60/976,648 filed Oct. 1, 2007, and entitled "Intraatrial Ventricular Assist Device," the contents of each being incorporated herein by reference in their entireties for all purposes.

BACKGROUND

Over 50,000 people die each year because of congestive heart failure, a condition that often cannot be treated with drug or surgical therapies. Moreover, nearly 550,000 new patients are diagnosed with congestive heart failure each year. For many patients that suffer heart failure, an attractive option is heart transplantation. The scarcity of suitable donor hearts has limited the impact of this therapy, however. As such, recent efforts have focused on the development of mechanical pumps to assist the failing heart. Fortunately, great strides have been made in the development of ventricular assist devices ("VADs"). Instead of totally replacing heart function, a VAD augments the existing heart's ability to pump blood. These devices have saved many patients who would not have survived without a heart transplant. Despite it success, current VAD technology still has much room for improvement. Specifically, there is a need for less invasive methods and devices that may be used to temporarily or permanently assist a failing human heart.

BRIEF SUMMARY

Novel methods and devices for assisting ventricular function of a heart are described herein. Embodiments of the device may be implanted within the atrium of a heart and comprises an outflow conduit that passes through the atrial septum. The outflow conduit may then pass through the superior vena cava, out the subclavian vein and be attached to a subclavian artery. Alternatively, the device may be placed down the jugular vein. The disclosed device foregoes the need for a pocket outside of the heart and further does not entail cutting a hole in the ventricle. Minimally invasive surgical techniques may be employed to implant embodiments of the device. Other aspects and features of the disclosed methods and devices will be described in more detail below.

Thus, embodiments comprise a combination of features and advantages that enable it to overcome the problems of prior devices. The foregoing has outlined rather broadly the features and technical advantages of the disclosed embodiments in order that the detailed description that follows may be better understood. Additional features and advantages will be described hereinafter that form the subject of the claims. It should be appreciated by those skilled in the art that the conception and the specific embodiments disclosed may be readily utilized as a basis for modifying or designing other structures for carrying out the same purposes. It should also be realized by those skilled in the art that such equivalent constructions do not depart from the spirit and scope of the disclosure.

BRIEF DESCRIPTION OF THE DRAWINGS

For a detailed description of the preferred embodiments, reference will now be made to the accompanying drawings in which.

NOTATION AND NOMENCLATURE

Figure 1:
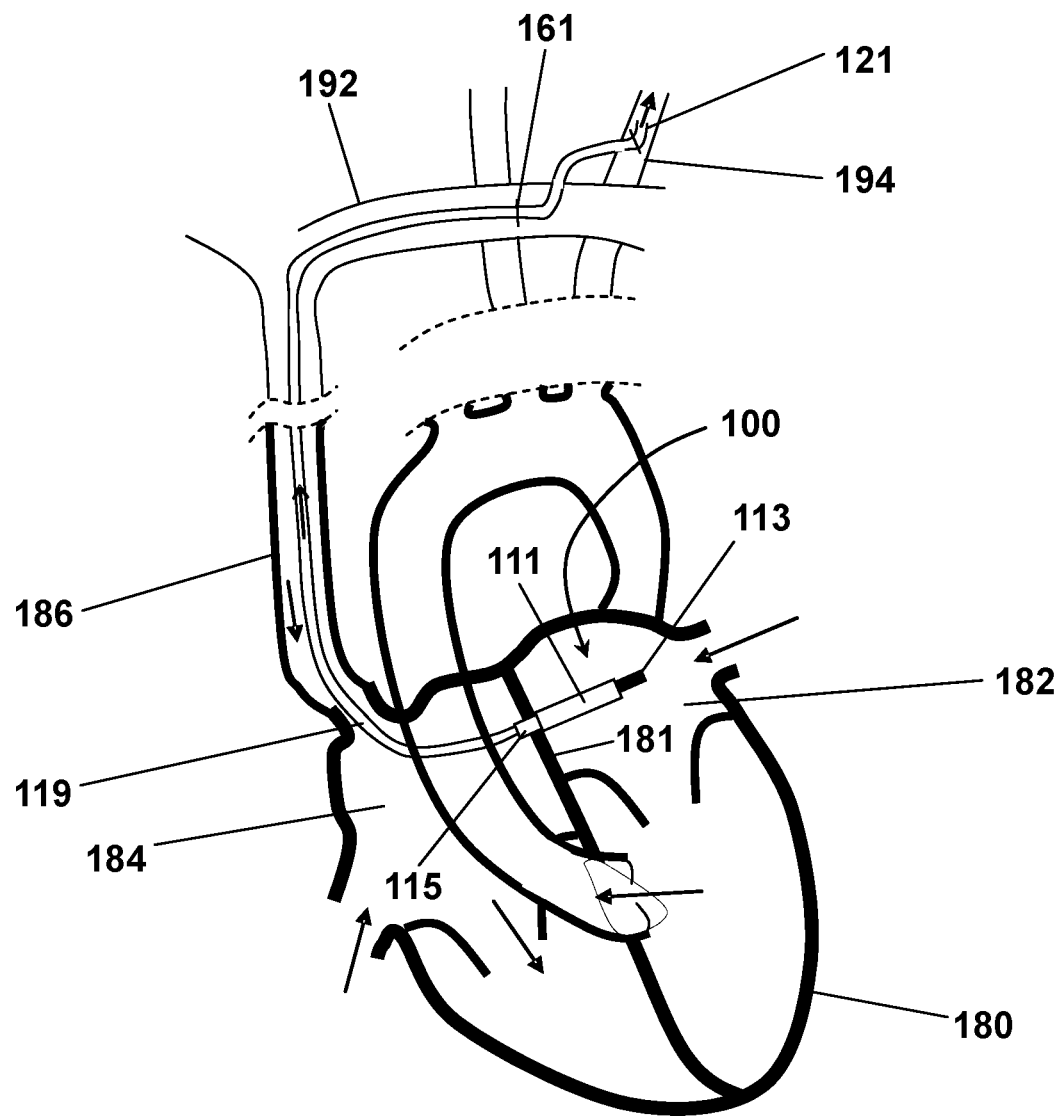
FIG. 1 illustrates an embodiment of a ventricular assist device (VAD) implanted in a heart.

Certain terms are used throughout the following description and claims to refer to particular system components. This document does not intend to distinguish between components that differ in name but not function. In the following discussion and in the claims, the terms "including" and "comprising" are used in an open-ended fashion, and thus should be interpreted to mean "including, but not limited to . . . ."

The term "continuous flow pump" is used to describe any pump which utilizes a rapidly spinning impeller or similar component to generate flow.

DETAILED DESCRIPTION OF THE PREFERRED EMBODIMENTS

VADs can be right VADs ("RVADs"), left VADs ("LVADs"), or both left and right VADs ("BiVADs") depending on which ventricle the VAD is designed to assist. In the past, LVAD's have been based on a pulsatile system in an effort to mimic the human heart. In recent years, research has focused on continuous flow systems as an alternative to the traditional pulsatile model. In a continuous flow system, blood is continuously pumped through the body rather than pulsing the blood rhythmically as in the human heart.

Continuous flow systems offer several advantages over pulsatile systems. First, continuous flow pumps are generally smaller than pulsatile pumps. Shrinking the size of artificial heart devices will allow doctors to treat women and small children who previously were not candidates for pulsatile LVADs. Second, continuous flow pumps consume less energy than pulsatile systems. This property is important for quality of life issues, allowing the device to run on smaller batteries. Finally, continuous flow pumps are mechanically much simpler; and have no flexible membranes or valves resulting in substantially improved endurance.

The field of LVADs is advancing rapidly. Like any new technology, results are improving with better device designs and increased experience. It is now becoming increasingly clear that in many patients, a pump with a rate 2 or 3 liters per minute may be of value in patients in whom early (class III) heart failure is present. By implanting such an assist device earlier in the course of the affliction, progression to class IV may be averted. Furthermore, in these earlier stage patients, it is quite probable that 2 or 3 liters of blood flow per minute may be all that is required to restore the patients to class I status.

If it is contemplated that pumps be placed in patients earlier in the course of their illness, it is imperative that it be done in a manner that minimizes invasiveness. As these patients are in no immediate peril, and can be managed for a time on medical therapy, a pump implantation procedure, if it is to be widely accepted and practiced, must be associated with relatively little morbidity and mortality.

To treat congestive failure and prevent, and possibly reverse, progression of cardiac derangements, a device needs to remove blood from the left side of the heart and deliver it into the systemic circulation in sufficient volumes that cardiac output is maintained or increased while left ventricular wall tension and work is decreased. One means is to introduce a cannula through the systemic veins, either subclavian, jugular, or femoral, and using conventional wire skills, position the tip across the atrial septum in the left atrium. Oxygenated blood removed from the left atrium through this cannula can then be returned by way of a cannula or graft attached to any systemic artery.

Figure 2:
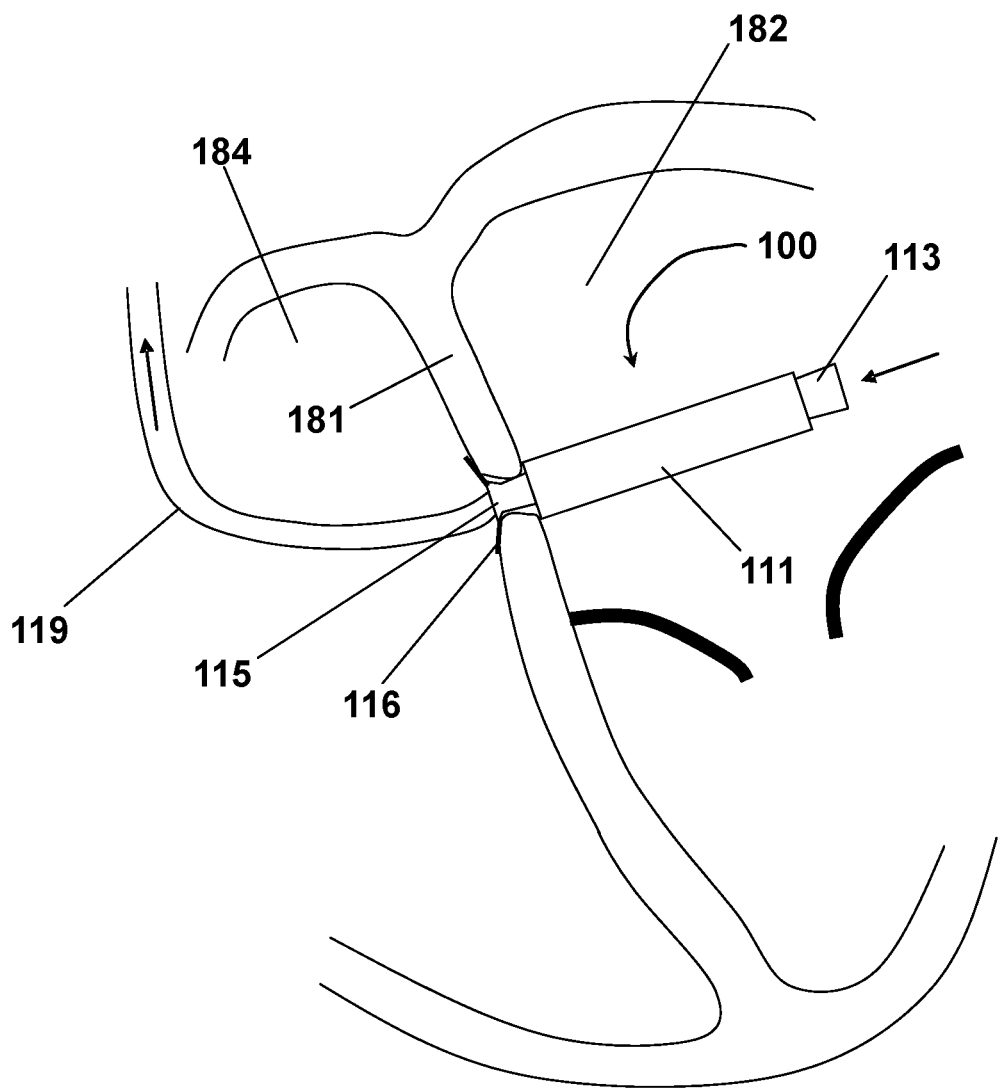
FIG. 2 illustrates a close-up of an embodiment of a VAD in the left atrium of a heart.

FIGS. 1 and 2 illustrate an embodiment of a device 100 configured specifically for limited access implantation without the need for cardiopulmonary bypass. In an embodiment, the device comprises a pump 111 adapted to be implanted within a heart atrium 182. Pump 111 has an inlet 113 and an outlet 115. A flexible conduit 119 may be coupled to the pump outlet. In addition, pump 111 has an expandable attachment collar 116 for attachment to the atrial septum 181 as shown in FIG. 2.

FIG. 1 also illustrates the configuration of an embodiment of the device as implanted within a human heart 180. Pump 111 may be attached to the wall or septum 181 dividing the right atrium 184 and left atrium 182 of the heart 180. Pump inlet 113 preferably is directed toward the center of the left atrium 182. Fresh oxygenated blood from the lungs enters the left atrium 182 and a portion may be sucked into the pump 111. Flexible outflow conduit 119 may pass interatrially through the septum 181 into the right atrium 184, up the superior vena cava 186, into the subclavian 192 vein or the ipsilateral jugular vein and through the subclavian vein or jugular vein wall 161. Preferably, flexible outflow conduit has a diameter no more than 9 mm and comprises a polymer of polyurethaneurea, polytetrafluoroethylene, polyethylene, polycarbonate, silicone, or combinations thereof. The proximal end 121 of conduit 119 may be anastomosed to the subclavian artery 194 or other suitable artery. Accordingly, the oxygenated blood from the left atrium 182 is sucked into pump and forced through conduit 119 into the subclavian artery 194 for recirculation of oxygenated blood to the body.

In relation to the superior vena cava, the flow in the conduit is countercurrent. Preferably, the pump 111 comprises pressure sensitive impellers. The impellers preferably comprise angled vanes, curved vanes, flexible vanes, tapered vanes, round vanes, propellers, open impellers, closed impellers, or any combination thereof.

Preferably, the pump 111 comprises a continuous flow pump. The pump 111 itself can be any one of a variety of designs, including without limitation, centrifugal, diagonal, or axial, and the external diameter of the pump, inclusive of the motor, preferably fits through a narrow sheath such as without limitation, a 24-French sheath. The pump 111 preferably provides 2-3 liters per minute of flow. The outlet 115 of the pump 111 may be a 7 or 8 mm graft of PTFE, Dacron, or other suitable material. The electrical driveline (not shown) of the pump 111 will preferably run in or closely adjacent to the outer wall of the outflow graft.

Figure 3:
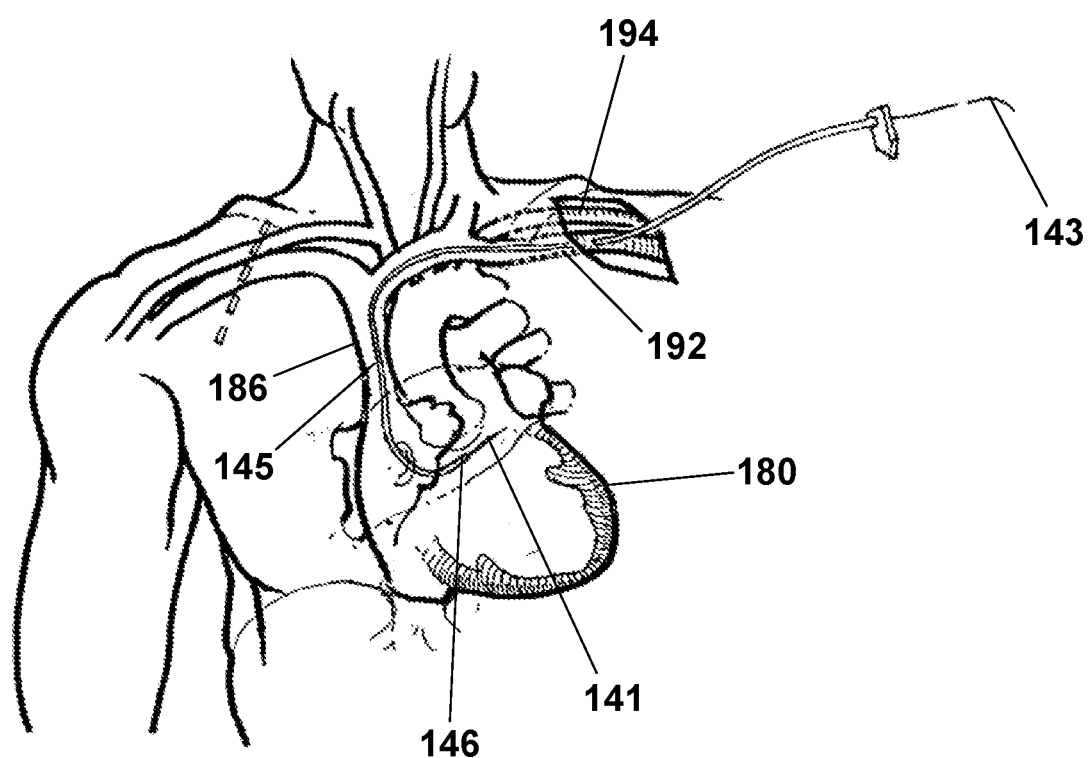
FIG. 3 illustrates an embodiment of a method of implanting the disclosed VAD in a heart.

In an embodiment of a method of assisting ventricular function of a heart, the disclosed device 100 may be implanted within a patient using novel surgical techniques as shown in FIGS. 2 and 3. More particularly, to implant embodiments of the device, a small incision may be made below the middle third of the clavicle. The subclavian artery 194 is identified and exposed, preferably on the left. A needle 141 is then introduced into the subclavian vein 192 or ipsilateral jugular vein, and a guide wire 143 is passed into the right atrium under fluoroscopic guidance. Catheters and surgical techniques may then be used to perform puncture of the atrial septum 181 and create guide wire access to the left atrium 182. A sheath 145 (e.g. thin-walled split-away 24-French sheath) may then be introduced into the left atrium 182 over a very flexible dilator that, despite flexibility, has adequate column stiffness to allow advancement. Fluoroscopy may be used to insure that the distal tip 146 of the sheath 145 is across the atrial septum 181. Alternatively, intravascular ultrasound may be used, the two imaging techniques may be used together, or other imaging modalities may be employed including but not limited to MRI, CT, and ultrasound.

Once in position, the dilator is removed and the pump 111 is placed down the sheath lumen, until the pump 111 itself is in the left atrium 182 with the inlet 113 projecting toward the center of the chamber. In one embodiment, a collar extending from the pump body that is constrained by the sheath is allowed to expand in the left atrium 182, which allows the pump 111 to be pulled back snuggly against the interatrial septum 181, minimizing hardware in the left atrium 182. In other embodiments, the collar is expanded by balloon catheter inflation, by pulling a suture, or by another mechanism.

To facilitate advancing the pump 111 down the sheath, an obturator may be placed down the lumen of the outflow graft. The obturator is preferably flexible to allow the pump 111 and outflow graft or conduit 119 to successfully navigate the sheath 145, but has sufficient column strength to allow advancement.

Once the pump 111 is in the left atrium 182, the sheath 145 is removed by splitting while using fluoroscopy to insure that the pump 111 does not dislodge. Once the sheath has been removed completely from the subclavian vein, the outflow graft and the pump driveline exits through the previously created venotomy in the ipsilateral subclavian or jugular vein. The outflow graft may be sutured the venotomy margin to prevent venous hemorrhage around the outflow graft. The distal end of the graft is beveled and sutured to the subclavian artery to deliver the blood flowing from pump 111 to the systemic circulation. The driveline is tunneled through the subcutaneous tissue to an appropriate site where it exits through the skin, and is attached to the power supply. Preferably, the outflow conduit passes retrograde through a lumen of systemic veins and exits through a wall of the systemic veins to allow the outflow conduit to be sutured, in an end-to-side fashion, to a systemic artery.

The device 100 and technique for implantation described here have several unique advantages. By positioning the pump 111 in the left atrium 182, the need for a pump pocket is eliminated, thereby reducing the likelihood of pump infection. Furthermore, the technique described above can be done without opening the chest, through a superficial incision, and does not require cardiopulmonary bypass. As the pump 111 is pulled flush against the left side of the atrial septum 181, the amount of material protruding into the left atrium 182 is minimized. This geometric arrangement also reduces the length of the pump blood path, which extends from the atrial septum 181 to the left subclavian artery, and facilitates a non-kinking lay of the outflow graft. By placing the pump 111 directly in the left atrium 182, it is possible that the likelihood of thrombus formation will be less due to high velocity flow entering the pump 111. As the outflow graft will come off the back of the pump 111 in a linear coaxial geometry, obtaining acceptable pump and graft lie should be facilitated. Although the patient may develop narrowing or even occlusion of the subclavian or jugular vein, this is generally well tolerated, and it is possible that outflow grafts of appropriate size or composed of appropriate material on the external surface may minimize this occurrence.

Figure 4:
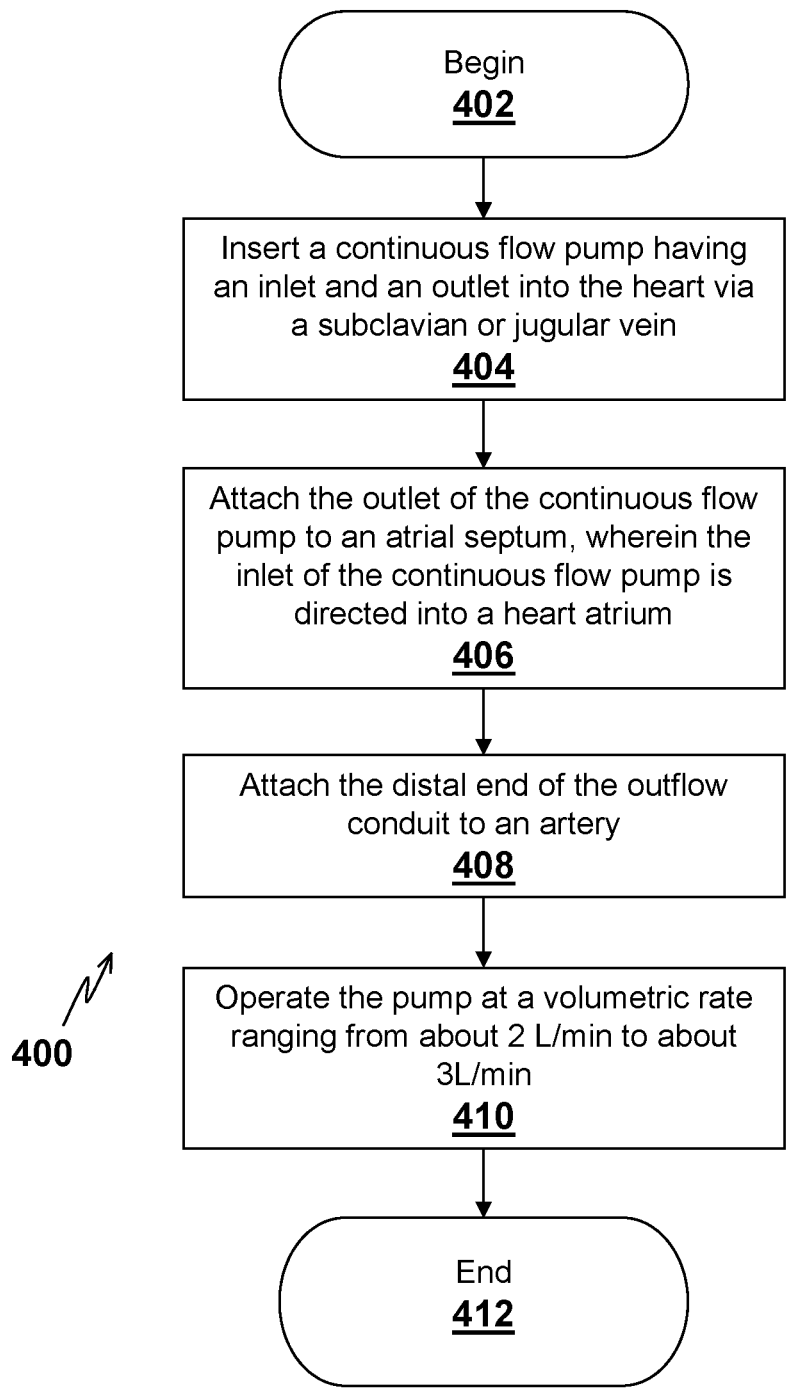
FIG. 4 illustrates a method of assisting ventricular function of a heart of a patient.

FIG. 4 illustrates a method 400 of assisting ventricular function of a heart of a patient beginning at 402 and ending at 412. At 404, a continuous flow pump having an inlet and an outlet is inserted into the heart via a subclavian or jugular vein. At 406, the outlet of the continuous flow pump is attached to an atrial septum, wherein the inlet of the continuous flow pump is directed into a heart atrium. At 408, the distal end of the outflow conduit is attached to an artery. At 410, the pump is operated at a volumetric rate ranging from about 2 L/min to about 3 L/min.

Figure 5:
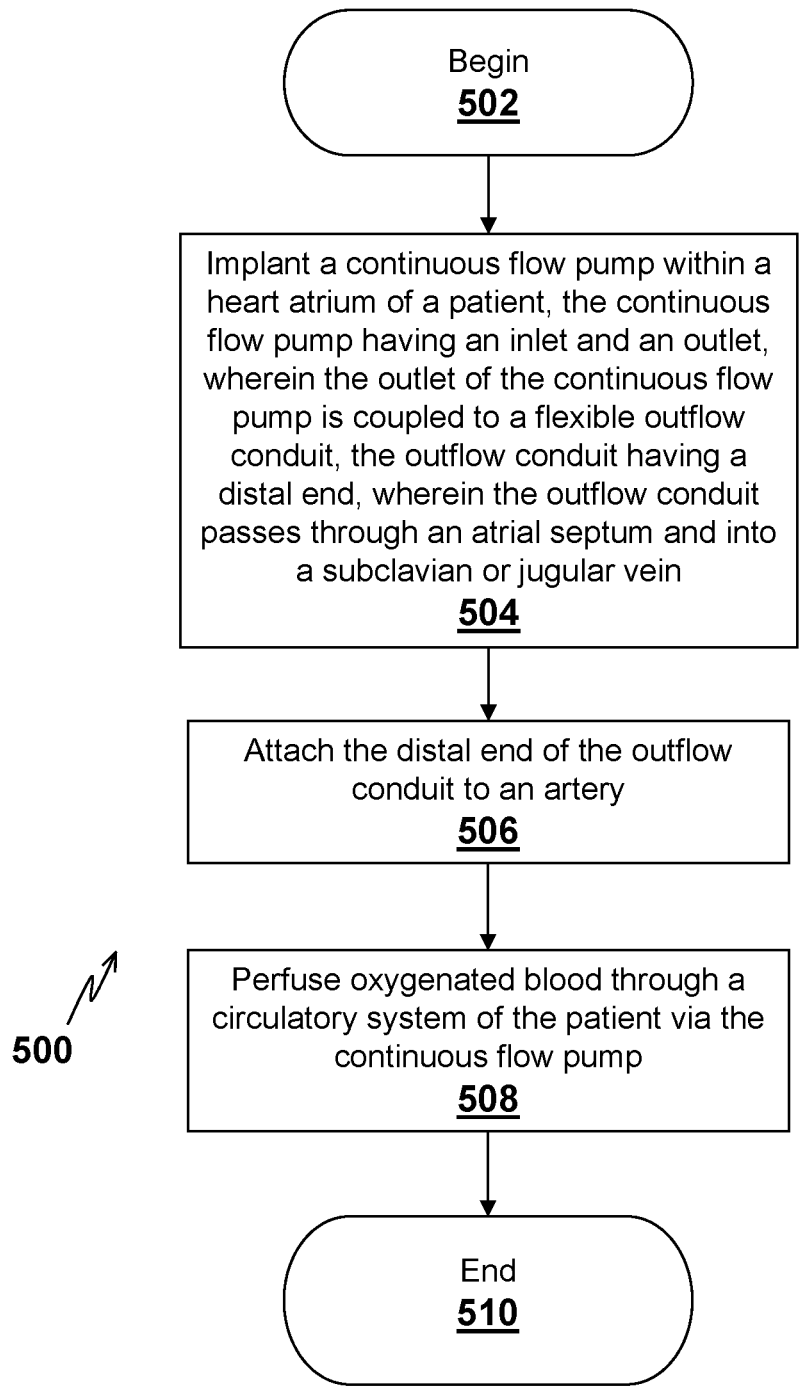
FIG. 5 illustrates a method of assisting ventricular function of a heart.

FIG. 5 illustrates a method 500 of assisting ventricular function of a heart beginning at 502 and ending at 510. At 504, a continuous flow pump is implanted within a heart atrium of a patient, the continuous flow pump having an inlet and an outlet, wherein the outlet of the continuous flow pump is coupled to a flexible outflow conduit, the outflow conduit having a distal end, wherein the outflow conduit passes through an atrial septum and into a subclavian or jugular vein. At 506, the distal end of the outflow conduit is attached to an artery. At 508, oxygenated blood is perfused through a circulatory system of the patient via the continuous flow pump.

In some embodiments, the driveline for the pump is routed along and through the wall of the outflow conduit such that separate routing of the driveline through the patient's body are avoided and the number of incisions required is reduced. For example, referring now to FIG. 6, another embodiment of a device 200 configured specifically for limited access implantation without the need of a cardiopulmonary bypass is shown. Device 200 is substantially similar to the device 100 previously described and shown in FIGS. 1 and 2. As a result, like reference numerals will be used to refer to components that are shared between devices 100, 200 and the discussion below will focus on the components and features of device 200 that are different from device 100. Specifically, device 200 includes pump 111 being the same as previously described (note: expandable attachment collar 116 is not shown on pump 111 in FIG. 6 for convenience and so as not to unduly complicate the figure; however, collar 116 may be incorporated onto pump 111 in system 200 in the same manner as described above for system 100). As previously described, pump 111 includes an inlet 113 and an outlet 115 and is configured to be inserted within an atrium of a heart (e.g., right atrium 182 of heart 180 in FIGS. 1 and 6). For example, in some embodiments pump 111 has a total length $L_{111}$ (e.g., between inlet 113 and outlet 115) of about 30 mm or less, and a maximum outer diameter $D_{111}$ of about 8.5 mm or less.

Figure 6:
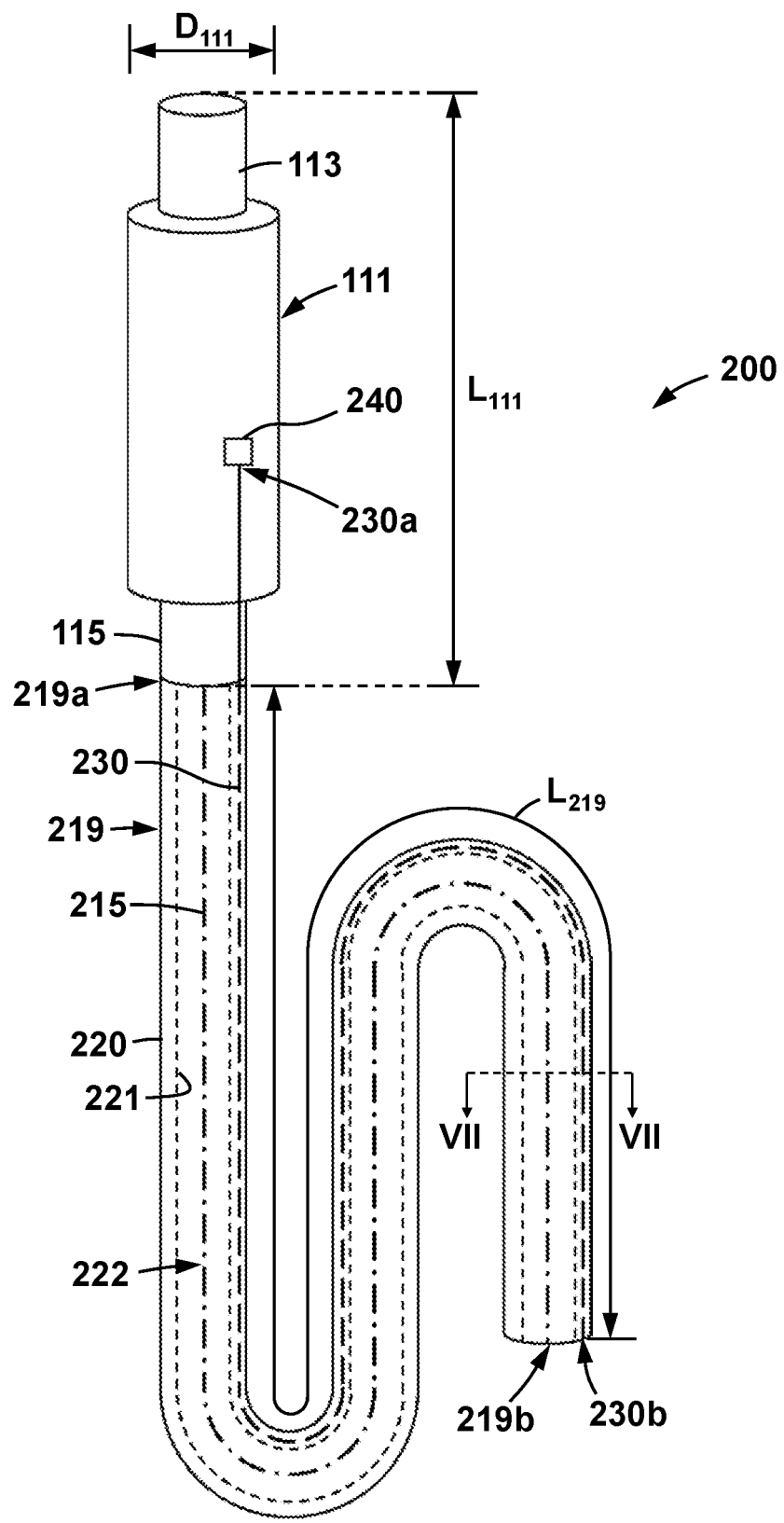
FIG. 6 is a perspective view that illustrates another embodiment of a VAD.

In addition, system 200 includes a physically flexible outflow conduit 219 that is coupled to outlet 115. As shown in FIG. 6, outflow conduit 219 includes a central or longitudinal axis 215, a first or proximal end 219a, a second or distal end 219b opposite proximal end 219a, a radially outer surface 220 extending between ends 219a, 219b, and a radially inner surface 221 extending between ends 219a, 219b. As used herein, the end 219a is referred to as a "proximal" end because it is proximal to pump 111 and the end 219b is referred to has a "distal" end because it is distal to pump 111. Radially inner surface 221 defines a continuous throughbore or lumen 222 extending between ends 219a, 219b such that when proximal end 219a of outflow conduit 219 is coupled to outlet 115 of pump 111, outlet 115 is placed in fluid communication with distal end 219b via throughbore. Outflow conduit 219 includes a total length $L_{219}$ extending axially between ends 219a, 219b that preferably ranges from 25 cm to 50 cm.

Figure 12:
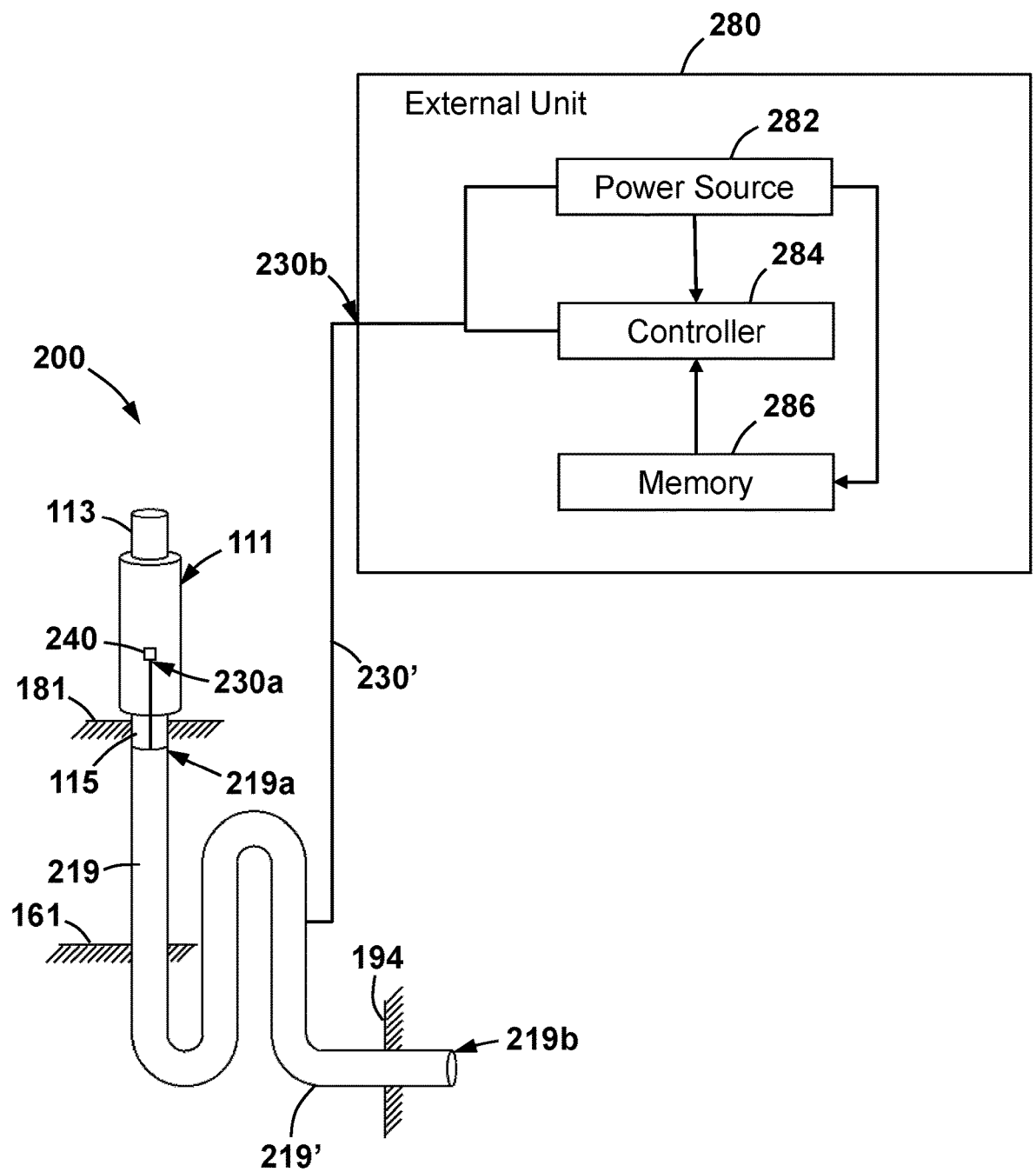
FIG. 12 illustrates a box diagram of the VAD of FIG. 6 and an external unit.

System 200 also includes a driveline 230 that is coupled to pump 111 and is configured to route control and power signals between pump 111 and a controller or other device (e.g., controller 284 in the external unit 280 shown in FIG. 12). In this embodiment, driveline 230 includes a first or proximal end 230a, and a second or distal end 230b opposite proximal end 230a. As previously described, in this embodiment, driveline 230 extends through the wall of the outflow conduit 219. More specifically, driveline 230 extends between radially outer surface 220 and radially inner surface 221 of outflow conduit 219. Thus, distal end 230b of driveline 230 is commensurate or proximate distal end 219b of outflow conduit 219.

In addition, proximal end 230a of driveline 230 is coupled to pump 111 at a connector 240. Connector 240 may comprise any suitable connector (e.g., a pin connector) that is configured to connect to a conductor (e.g., driveline 230). In this embodiment, connector 240 is shown disposed externally to pump 111; however, in other embodiments connector 240 is disposed internally within pump 111 and proximal end 230a of driveline 230 extends through a port or other suitable aperture to access connector 240. While not specifically shown, connector 240 is coupled to the internal electronic components of pump 111. For example, connector 240 is coupled to the motor that drives operation of pump 111 such that coupling proximal end 230a of driveline 230 to connector 240 also couples (e.g., electrically) driveline 230 to the motor of pump 111.

Figure 7:
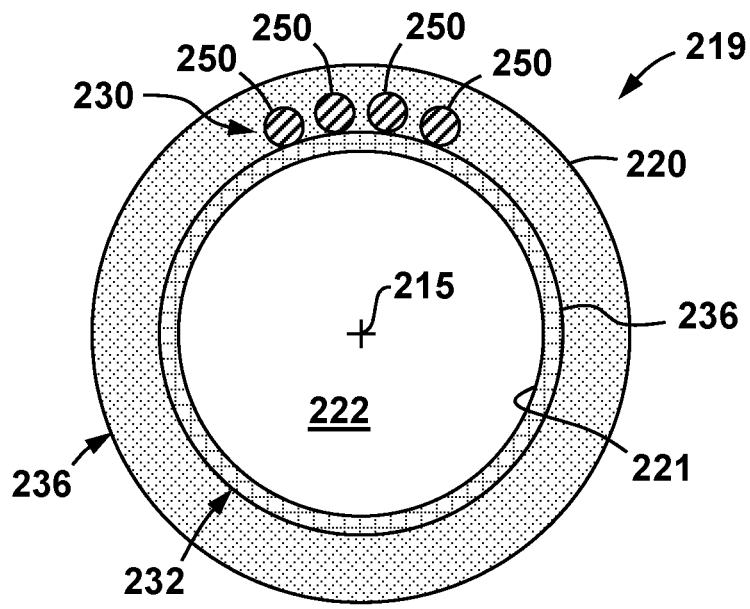
FIG. 7 is a cross-sectional view taken along section VII-VII in FIG. 6.

Referring now to FIG. 7, as previously described, driveline 230 is routed through the wall of outflow conduit 219, between radially outer surface 220 and radially inner surface 221. As shown in FIG. 7, in some embodiments, driveline 230 comprises one or more electrical conductors 250 that extend axially and generally parallel to one another between ends 230a, 230b and radially between surfaces 220, 221. It should be appreciated that in other embodiments driveline 230 may comprise only a single electrical conductor 250 or may comprise a single bundled cable housing a plurality of individual electrical conductors 250. In any event, in this embodiment electrical conductors 250 each comprise an electrically conductive material (e.g., a metal, conductive polymer, etc.) such that each is configured to conduct electrical signals between ends 230a, 230b. In other embodiments, conductors 250 may not be electrically conductive and may instead be configured to conduct some other form of energy signal, such as, for example, light signals (e.g., with driveline 230 comprising one or more fiber optic cables), acoustic signals, etc.

In addition, in this embodiment, a subset of the conductors 250 (e.g., two) may be utilized to carry electrical power signals between a power source (e.g., battery, capacitor, electric current from the public utility, etc.) and pump 111 top facilitate and drive operation of pump 111. In addition, another subset of the conductors 250 may be utilized to carry control and informational signals between pump 111 and a controller or other control unit (e.g., controller 284 in the external unit 280 shown in FIG. 12). For example, one of the conductors 250 may carry a control signal from the controller to the pump 111 that causes the pump 111 to produce blood from the outlet 115 at a desired rate (e.g., in a given unit volume per unit time). As another example, one of the conductors 250 may carry an informational signal from the pump 111 to the controller that indicates some physical condition of the pump 111 (e.g., the rotational rate of the impeller, the internal pressure or temperature of the pump 111, the vibration experienced by the pump 111, etc.).

Figure 8:
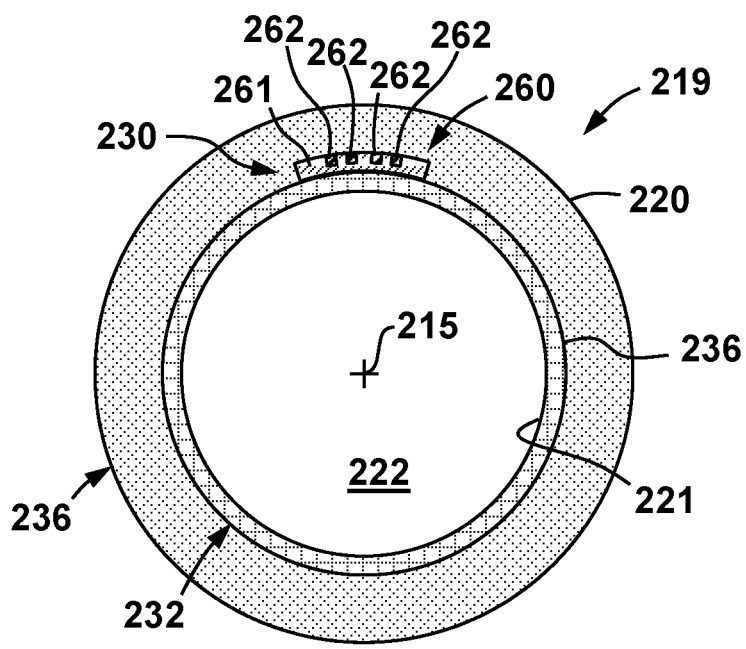
FIG. 8 is a cross-sectional view taken along section VII-VII in FIG. 6 of another embodiment of the VAD.

Referring now to FIG. 8, in some embodiments, driveline 230 may comprise physically flexible circuit 260 that includes a plurality of individual conductive lines 262 etched or otherwise formed on a substrate 261. Conductive lines 262 may be formed of any suitable electrically conductive material such as for example a metal or conductive polymer. Substrate 261 may comprise a physically flexible (e.g., rollable, bendable, foldable, etc.) and electrically insulating material such as, for example, a polymer.

As with conductors 250 previously described, a subset of the conductive lines 262 (e.g., two) may be utilized to carry electrical power signals between a power source (e.g., battery, capacitor, electric current from the public utility, etc.) and pump 111 to facilitate and drive operation of pump 111. In addition, another subset of the conductive lines 262 may be utilized to carry control and informational signals between pump 111 and a controller or other control unit (e.g., controller 284 in the external unit 280 shown in FIG. 12). For example, one of the conductive lines 262 may carry a control signal from the controller to the pump 111 that causes the pump 111 to produce blood from the outlet 115 at a desired rate (e.g., in a given unit volume per unit time). As another example, one of the conductive lines 262 may carry an informational signal from the pump 111 to the controller that indicates some physical condition of the pump 111 (e.g., the rotational rate of the impeller, the internal pressure or temperature of the pump 111, the vibration experienced by the pump 111, etc.).

Referring now to FIGS. 7 and 8, regardless of the type of driveline 230 used (e.g., conductors 250 or flexible circuit 260), driveline 230 is disposed radially between a first or inner tubular layer 232 defined within outflow conduit 219 and a second or outer tubular layer 236 defined within outflow conduit 219. Inner tubular layer 232 includes radially inner surface 221 and therefore defines throughbore 222, and outer tubular member includes radially outer surface 220. During manufacturing of outflow conduit 219, driveline 230 is disposed along a radially outermost surface 234 of inner layer 232, and then outer layer 236 is disposed about inner layer 232 and driveline 230 such that driveline 230 is captured (e.g., laminated) between layers 232, 236 as shown. Preferably each of the inner layer 232 and outer layer 236 comprise electrically insulating materials (e.g., polymers, elastomers, etc.). In addition, at least inner layer 232 (and perhaps also outer layer 236 in some embodiments) comprises a fluid tight material that is configured to restrict (if not prevent) leakage of blood or other bodily fluids therethrough. In this embodiment, outer layer 236 comprises polytetrafluoroethylene (PTFE), and inner layer 232 comprises expanded PTFE (ePTFE).

Figure 9:
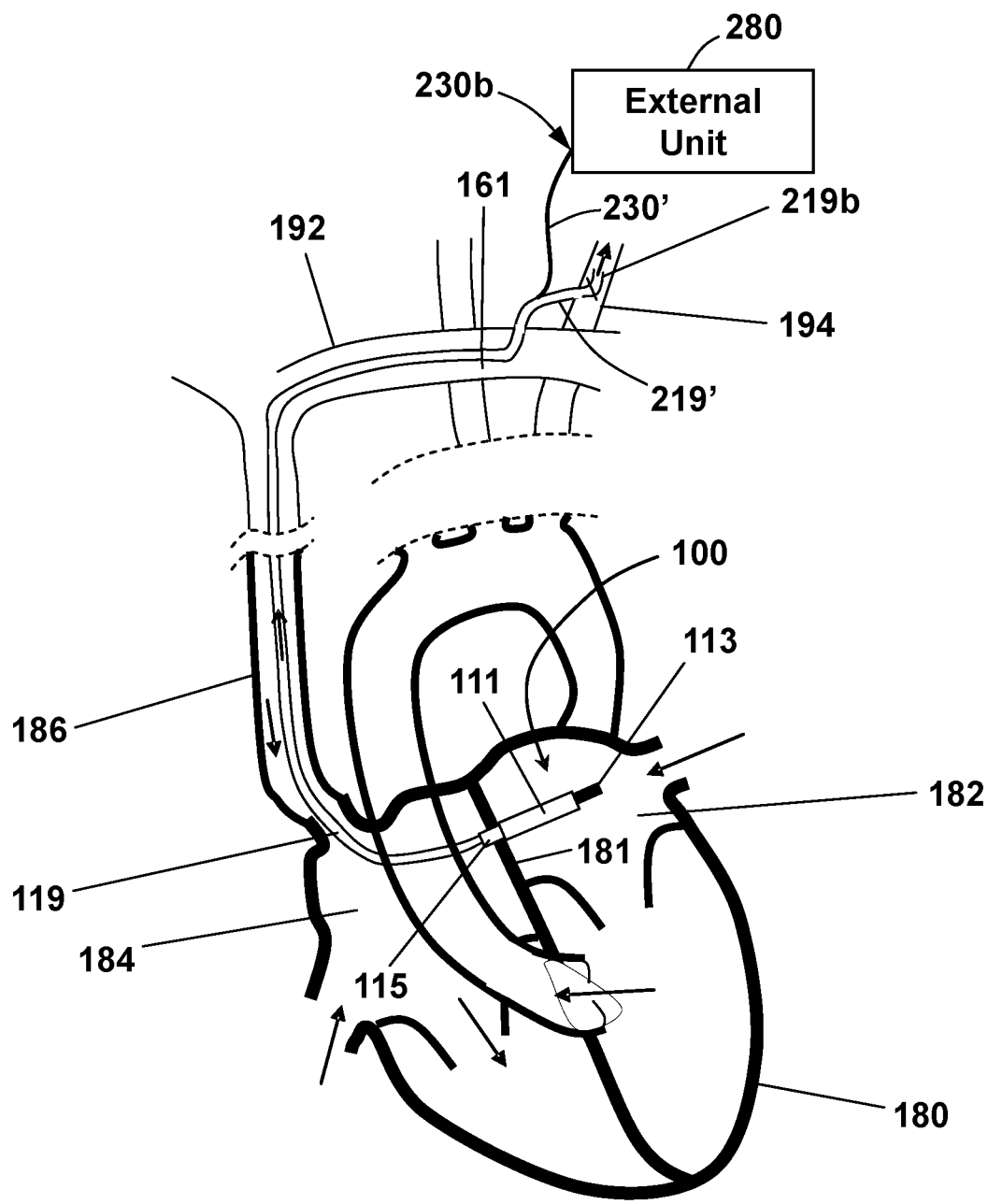
FIG. 9 illustrates the VAD of FIG. 6 implanted in a heart.
Figure 10:
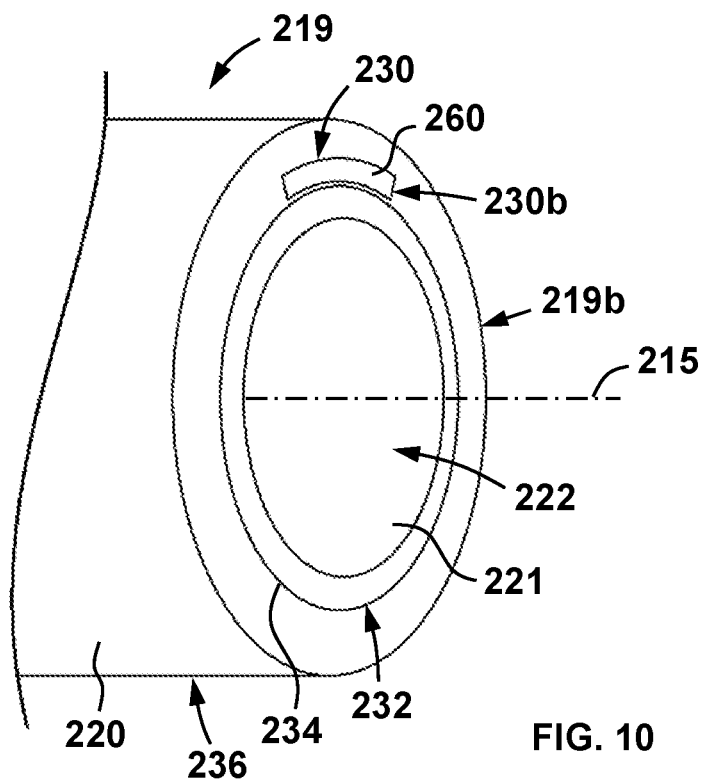
FIGS. 10 and 11 illustrate sequential, perspective views of the driveline being peeled away from the outflow conduit of the VAD device of FIG. 6.
Figure 11:
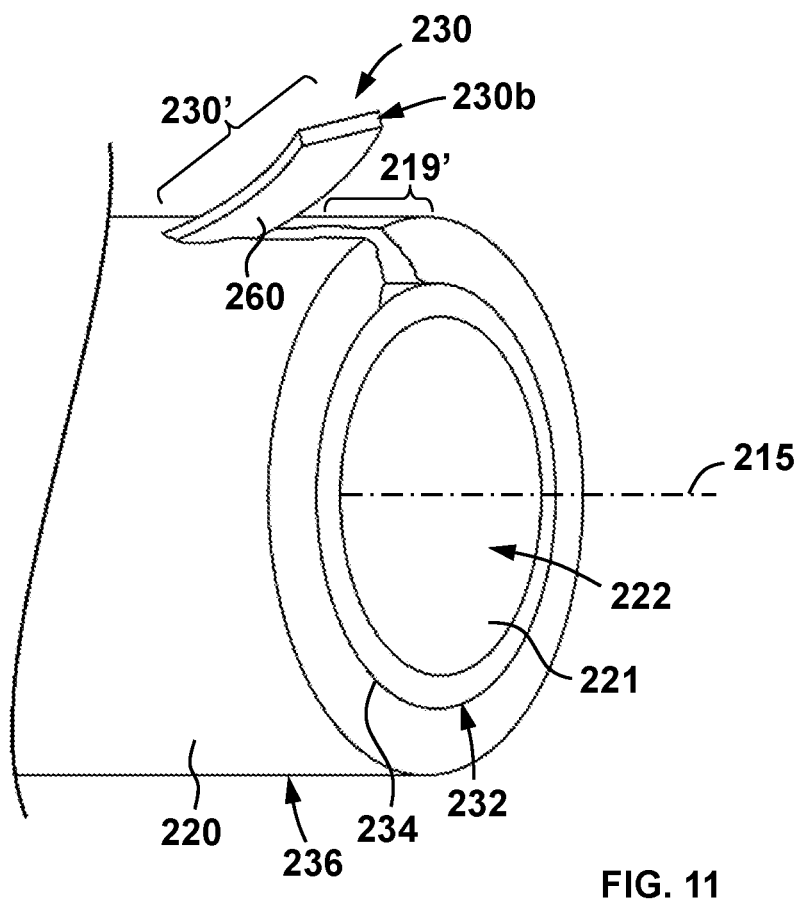

Referring now to FIG. 9, in an embodiment of a method of assisting ventricular function of a heart, the disclosed device 200 may be implanted within a patient in substantially the same manner as shown and discussed for system 100. However, because driveline 230 is disposed within outflow conduit 219, driveline 230 is carried along conduit 219 back through the subclavian vein or jugular vein wall 161 and the original incision below the middle third of the clavicle. Thereafter, the driveline 230 may be peeled or otherwise separated from outflow conduit 219 from the distal end 219b, and the portion 219' of conduit 219 that is separated from driveline 230 may be inserted into an artery (e.g., the subclavian artery 194) as previously described above. Specifically, referring briefly to FIGS. 10 and 11, during these operations, distal end 230b of driveline 230 may be grasped and pulled radially away from inner tubular layer 232 and through outer tubular layer 236 such that a portion 230' of driveline 230 may be peeled away from inner and outer tubular layers 232, 236, respectively (note: while FIGS. 10 and 11 show driveline 230 having the flexible circuit 260, it should be appreciated that a similar peeling operation may be accomplished when the driveline comprises the conductors 250). Referring back now to FIG. 9, following the partial separation of driveline 230 from outflow conduit 219, the separated portion 230' of driveline 230 (which includes distal end 230b) is routed outside of the body toward an external unit 280, so that distal end 230b may be connected or otherwise coupled to external unit 280.

Referring now to FIG. 12, a block diagram of system 200, including external unit 280 is shown. As shown in the example of FIG. 12, the external unit 280 includes a power source 282, a controller 284, and a memory 286. The power source 282 may comprise a battery (disposable or rechargeable), a capacitor, a wireless power receiver (e.g., inductive coil, etc.), or other sources of electrical power (e.g., power delivered from the local utility). The power source 282 provides electrical power to pump 111 via driveline 230 and to the other components within external device 280 (e.g., controller 284, memory 286, etc.). The controller 284 executes software provided on memory 286, and upon executing the software on memory 286 provides the external device 280 with all of the functionality described herein. The memory 286 may comprise volatile storage (e.g., random access memory), non-volatile storage (e.g., flash storage, read only memory, etc.), or combinations of both volatile and non-volatile storage. Data consumed or produced by the software can also be stored on memory 286. For example, measured data (e.g., pressure, temperature, etc. from inside pump 111) may be stored on memory 286. During operations, control signals and power signals are routed to pump 111 from controller 284 and power source 282, respectively, via driveline 230 in the manner previously described.

Figure 13:
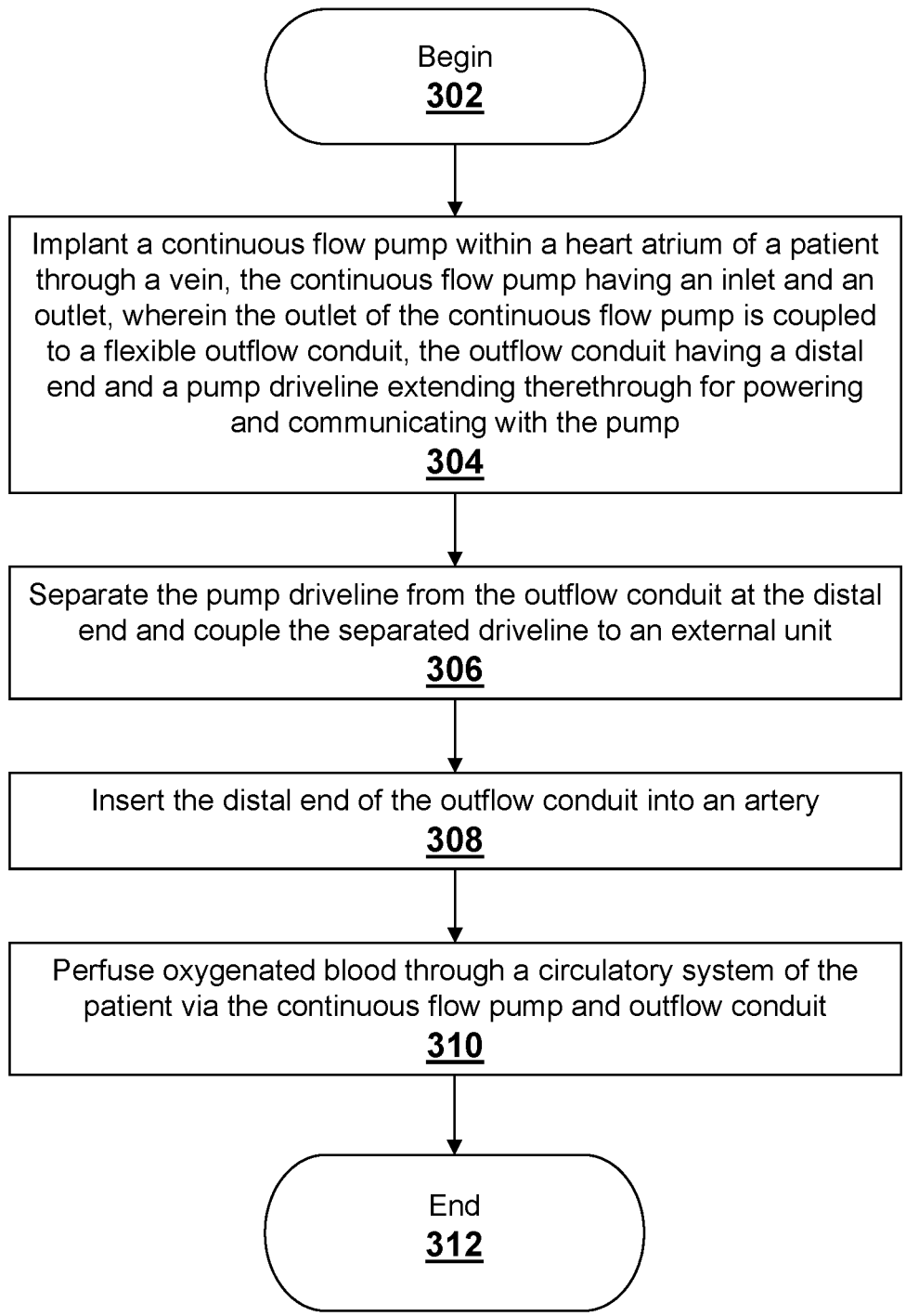
FIG. 13 illustrates a method of assisting ventricular function of a heart.

FIG. 13 illustrates a method 300 of assisting ventricular function of a heart beginning at 302 and ending at 312. At 304, a continuous flow pump (e.g., pump 111) is implanted within a heart atrium of a patient, the continuous flow pump having an inlet (e.g., inlet 113) and an outlet (e.g., outlet 115), wherein the outlet of the continuous flow pump is coupled to a flexible outflow conduit (e.g., outflow conduit 219), the outflow conduit having a distal end and a pump driveline (e.g., driveline 230) extending through the wall of the outflow conduit for powering and communicating with the pump. At 306, the driveline is separated from the outflow conduit at the distal end of the outflow conduit and the separated portion of the driveline is coupled to an external unit (e.g., external unit 280) which may include a controller (e.g., controller 284) and/or a power source (e.g., power source 282) for operating the pump. At 310, the distal end of the outflow conduit, having been separated from the driveline at 306, is inserted into an artery (e.g., the subclavian artery 194). Finally, at 310, oxygenated blood is perfused through a circulatory system (via the artery in 306) of the patient via the continuous flow pump.

The device 200 and technique for implantation described here have several unique advantages, many of which are shared with device 100 (and its associated implantation technique). For example, as with device 100, by positioning the pump 111 in device 200 in the left atrium 182, the need for a pump pocket is eliminated, thereby reducing the likelihood of pump infection. As another example, as with device 100, the technique involving device 200 described above can be done without opening the chest, through a superficial incision, and does not require cardiopulmonary bypass. Still further, the device 200 presents several additional advantages. For example, because driveline 230 is routed through the wall of outflow conduit 219, no additional tunneling or incisions need to be made to route driveline 230 to external unit 280. Therefore, the risk of infection and complications following the installation of device 200 within a patient is minimized.

While embodiments have been shown and described, modifications thereof can be made by one skilled in the art without departing from the spirit and teachings of the disclosure. The embodiments described and the examples provided herein are exemplary only, and are not intended to be limiting. Many variations and modifications of the embodiments disclosed herein are possible and are within the scope of the invention. Accordingly, the scope of protection is not limited by the description set out above, but is only limited by the claims which follow, that scope including all equivalents of the subject matter of the claims.

The discussion of a reference in the Description of the Related Art is not an admission that it is prior art, especially any reference that may have a publication date after the priority date of this application. The disclosures of all patents, patent applications, and publications cited herein are hereby incorporated herein by reference in their entirety, to the extent that they provide exemplary, procedural, or other details supplementary to those set forth herein.

What is claimed is:

1. A medical device comprising:
a pump configured to be inserted within an atrium of a heart, said pump comprising an inlet and an outlet;
a flexible outflow conduit coupled to the outlet and configured to carry blood, wherein the outflow conduit includes a radially inner surface defining a through-bore, and a radially outer surface; and
a driveline coupled to the pump and configured to conduct control and power signals between the pump and an external device, wherein the driveline extends through the outflow conduit between the radially inner surface and the radially outer surface.

2. The medical device of claim 1, wherein the outflow conduit comprises:
an inner tubular layer, wherein the inner tubular layer includes the radially inner surface; and
an outer tubular layer, wherein the outer tubular layer includes the radially outer surface;
wherein the driveline is disposed between the inner tubular layer and the outer tubular layer.

3. The medical device of claim 2, wherein the driveline is configured to be peeled away from the inner tubular layer.

4. The medical device of claim 2, wherein each of the inner tubular layer and the outer tubular layer comprise electrically insulating materials.

5. The medical device of claim 4, wherein the outer tubular layer comprises polytetrafluoroethylene (PTFE), and the inner tubular layer comprises expanded PTFE (ePTFE).

6. The medical device of claim 1, wherein the driveline comprises a plurality of individual electrical conductors.

7. The medical device of claim 1, wherein the driveline comprises a physically flexible circuit, that includes a plurality of conductive lines etched onto a substrate.

8. A method of assisting ventricular function of a heart of a patient comprising:
inserting a pump into the heart via a vein, wherein the pump includes an outlet that is coupled to a flexible outflow conduit, wherein the outflow conduit includes a distal end, a radially inner surface defining a through-bore, and a radially outer surface, outflow conduit housing a driveline between the radially inner surface and the radially outer surface, the driveline coupled to the pump;
extending the outflow conduit through the vein;
separating a portion of the driveline from the outflow conduit;
coupling the portion of the driveline to an external unit;
inserting the distal end of the outflow conduit to an artery; and
operating the pump with control and power signals conducted through the driveline to induce blood flow through the flexible outflow conduit.

9. The method of claim 8, wherein separating the portion of the driveline from the outflow conduit comprises peeling the portion of the driveline away from the outflow conduit from the distal end of the outflow conduit.

10. The method of claim 8, wherein coupling the portion off the driveline to an external unit comprises coupling the portion of the driveline to at least one of a controller and a power source disposed within the external unit.

11. The method of claim 8, further comprising perfusing oxygenated blood into the artery through the pump and outflow conduit during the operating of the pump.

* * * * *